(12) United States Patent
Ma et al.

(10) Patent No.: US 9,808,439 B2
(45) Date of Patent: *Nov. 7, 2017

(54) USE OF TANGERETIN IN CANCER TREATMENT

(71) Applicant: Macau University of Science and Technology, Macau (CN)

(72) Inventors: Wen-zhe Ma, Macau (CN); Sen-ling Feng, Macau (CN); Xiao-jun Yao, Macau (CN); Zhong-wen Yuan, Macau (CN); Liang Liu, Macau (CN); Ying Xie, Macau (CN)

(73) Assignee: Macau University of Science and Technology, Macau (CN)

( * ) Notice: Subject to any disclaimer, the term of this patent is extended or adjusted under 35 U.S.C. 154(b) by 22 days.

This patent is subject to a terminal disclaimer.

(21) Appl. No.: 14/848,360

(22) Filed: Sep. 9, 2015

(65) Prior Publication Data

US 2017/0027900 A1 Feb. 2, 2017

Related U.S. Application Data

(60) Provisional application No. 62/198,141, filed on Jul. 29, 2015.

(51) Int. Cl.
*A61K 31/352* (2006.01)
*A61K 31/337* (2006.01)
*A61K 45/06* (2006.01)
*A61K 31/704* (2006.01)

(52) U.S. Cl.
CPC .......... *A61K 31/352* (2013.01); *A61K 31/337* (2013.01); *A61K 31/704* (2013.01); *A61K 45/06* (2013.01)

(58) Field of Classification Search
CPC ............................ A61K 31/352; A61K 31/337
See application file for complete search history.

(56) References Cited

FOREIGN PATENT DOCUMENTS

FR CA 2337179 A1 * 1/2000 ........... A61K 31/352

OTHER PUBLICATIONS

Arafa et al., Cancer Res., 2009, 69(23), p. 8910-8917.*
Gupta et al., Med. Chem. Res., 2014, 23, p. 1-15, published online May 16, 2013.*
Xing, H., et al., Activation of fibronectin/PI-3K/Akt2 leads to chemoresistance to docetaxel by regulating survivin protein expression in ovarian and breast cancer cells. Cancer Lett, 2008. 261(1): p. 108-19.
Geney, R., et al., Overcoming multidrug resistance in taxane chemotherapy. Clin Chem Lab Med, 2002. 40(9): p. 918-25.
Vasiliou, V., K. Vasiliou, and D.W. Nebert, Human ATP-binding cassette (ABC) transporter family. Hum Genomics, 2009. 3(3): p. 281-90.
Perez-Tomas, R., Multidrug resistance: retrospect and prospects in anti-cancer drug treatment. Curr Med Chem, 2006. 13(16): p. 1859-76.
Gottesman, M.M., T. Fojo, and S.E. Bates, Multidrug resistance in cancer: role of ATP-dependent transporters. Nat Rev Cancer, 2002. 2(1): p. 48-58.
Gianni, L., Anthracycline resistance: the problem and its current definition. Semin Oncol, 1997. 24(4 Suppl 10): p. S10-11-S10-17.
Ambudkar, S.V., et al., P-glycoprotein: from genomics to mechanism. Oncogene, 2003. 22(47): p. 7468-85.
Thomas, H. and H.M. Coley, Overcoming multidrug resistance in cancer: an update on the clinical strategy of inhibiting p-glycoprotein. Cancer Control, 2003. 10(2): p. 159-65.
Bansal, T., et al., Emerging Significance of Flavonoids as P-Glycoprotein Inhibitors in Cancer Chemotherapy. Journal of Pharmacy and Pharmaceutical Sciences, 2009. 12(1): p. 46-78.
Karthikeyan, S. and S.L. Hoti, Development of Fourth Generation ABC Inhibitors from Natural Products: A Novel Approach to Overcome Cancer Multidrug Resistance. Anticancer Agents Med Chem, 2015. 15(5): p. 605-615.
Alvarez, A.I., et al., Modulation of the activity of ABC transporters (P-glycoprotein, MRP2, BCRP) by flavonoids and drug response. J Pharm Sci, 2010. 99(2): p. 598-617.
Li, Y., et al., Interactions of dietary phytochemicals with ABC transporters: possible implications for drug disposition and multidrug resistance in cancer. Drug Metab Rev, 2010. 42(4): p. 590-611.
Morris, M.E. and S. Zhang, Flavonoid-drug interactions: effects of flavonoids on ABC transporters. Life Sci, 2006. 78(18): p. 2116-30.
Nogata, Y., et al., Flavonoid composition of fruit tissues of citrus species. Biosci Biotechnol Biochem, 2006. 70(1): p. 178-92.
Chen, J., et al., Nobiletin suppresses cell viability through AKT pathways in PC-3 and DU-145 prostate cancer cells. BMC Pharmacol Toxicol, 2014. 15:59.
Kim, M.S., et al., Tangeretin stimulates glucose uptake via regulation of AMPK signaling pathways in C2C12 myotubes and improves glucose tolerance in high-fat diet-induced obese mice. Mol Cell Endocrinol, 2012. 358(1): p. 127-34.
Meiyanto, E., A. Hermawan, and Anindyajati, Natural products for cancer-targeted therapy: citrus flavonoids as potent chemopreventive agents. Asian Pac J Cancer Prev, 2012. 13(2): p. 427-36.
Ho, S.C. and C.C. Lin, Investigation of heat treating conditions for enhancing the anti-inflammatory activity of citrus fruit (*Citrus reticulata*) peels. J Agric Food Chem, 2008. 56(17): p. 7976-82.
Pan, M.H., et al., Tangeretin induces cell-cycle G1 arrest through inhibiting cyclin-dependent kinases 2 and 4 activities as well as elevating Cdk inhibitors p21 and p27 in human colorectal carcinoma cells. Carcinogenesis, 2002. 23(10): p. 1677-1684.

(Continued)

*Primary Examiner* — Jonathan S Lau
(74) *Attorney, Agent, or Firm* — Eagle IP Limited; Jacqueline C. Lui

(57) ABSTRACT

The present invention discloses a pharmaceutical composition of treating multidrug resistance cancer, comprising a citrus methoxyflavone and a chemotherapeutic drug, in which the citrus methoxyflavone is tangeretin. A method of treating multidrug resistance cancer comprising administrating citrus methoxyflavone and a chemotherapeutic drug is also disclosed.

8 Claims, 10 Drawing Sheets
(7 of 10 Drawing Sheet(s) Filed in Color)

(56) References Cited

OTHER PUBLICATIONS

Morley, K.L., P.J. Ferguson, and J. Koropatnick, Tangeretin and nobiletin induce G1 cell cycle arrest but not apoptosis in human breast and colon cancer cells, Cancer Lett. 2007. 251:p. 168-178.
Arafa, E.S.A., et al., Tangeretin Sensitizes Cisplatin-Resistant Human Ovarian Cancer Cells through Down-regulation of Phosphoinositide 3-Kinase/Akt Signaling Pathway. Cancer Research, 2009. 69(23): p. 8910-8917.
Meiyanto, E., et al., The improvement of doxorubicin activity on breast cancer cell lines by tangeretin through cell cycle modulation. Oriental Pharmacy and Experimental Medicine, 2011. 11(3): p. 183-190.
Takanaga, H., et al., Polymethoxylated flavones in orange juice are inhibitors of P-glycoprotein but not cytochrome P450 3A4. J Pharmacol Exp Ther, 2000. 293(4): p. 230-6.
Honda, Y., et al., Effects of grapefruit juice and orange juice components on P-glycoprotein- and MRP2-mediated drug efflux. Br J Pharmacol, 2004. 143(7): p. 856-64.
Ohtani, H., et al., Effects of various methoxyflavones on vincristine uptake and multidrug resistance to vincristine in P-gp-overexpressing K562/ADM cells. Pharmaceutical Research, 2007. 24(10): p. 1936-1943.
Patino, W.D., et al., Circulating transcriptome reveals markers of atherosclerosis. Proc Natl Acad Sci U S A, 2005. 102(9): p. 3423-8.
Chou, T.C., Drug Combination Studies and Their Synergy Quantification Using the Chou-Talalay Method. Cancer Research, 2010. 70(2): p. 440-446.
Van Breemen, R.B. and Y. Li, Caco-2 cell permeability assays to measure drug absorption. Expert Opin Drug Metab Toxicol, 2005. 1(2): p. 175-85.
Ding, P.R., et al., The Phosphodiesterase-5 Inhibitor Vardenafil Is a Potent Inhibitor of ABCB1/P-Glycoprotein Transporter. Plos One, 2011. 6(4): e19329.
Wang, Y.J., et al., Motesanib (AMG706), a potent multikinase inhibitor, antagonizes multidrug resistance by inhibiting the efflux activity of the ABCB1. Biochem Pharmacol, 2014. 90(4): p. 367-78.
Aller, S.G., et al., Structure of P-glycoprotein reveals a molecular basis for poly-specific drug binding. Science, 2009. 323(5922): p. 1718-22.
Ohnishi, H., et al., Inhibition of cell proliferation by nobiletin, a dietary phytochemical, associated with apoptosis and characteristic gene expression, but lack of effect on early rat hepatocarcinogenesis in vivo. Cancer Sci, 2004. 95(12): p. 936-42.
Srivalli, K.M.R. and P.K. Lakshmi, Overview of P-glycoprotein inhibitors: a rational outlook. Brazilian Journal of Pharmaceutical Sciences, 2012. 48(3): p. 353-367.
Vinod, B.S., T.T. Maliekal, and R.J. Anto, Phytochemicals as Chemosensitizers: From Molecular Mechanism to Clinical Significance. Antioxidants & Redox Signaling, 2013. 18(11): p. 1307-1348.
Walle, T., Methoxylated flavones, a superior cancer chemopreventive flavonoid subclass? Semin Cancer Biol, 2007. 17(5): p. 354-62.
Wesolowska, O., et al., Multidrug Resistance Reversal and Apoptosis Induction in Human Colon Cancer Cells by Some Flavonoids Present in Citrus Plants. Journal of Natural Products, 2012. 75(11): p. 1896-1902.
Evans, M., P. Sharma, and N. Guthrie, Bioavailability of Citrus Polymethoxylated Flavones and Their Biological Role in Metabolic Syndrome and Hyperlipidemia, Readings in Advanced Pharmacokinetics—Theory, Methods and Applications, A. Noreddin, Editor. 2012.
Manthey, J.A., et al., Pharmacokinetic study of nobiletin and tangeretin in rat serum by high-performance liquid chromatography-electrospray ionization-mass spectrometry. J Agric Food Chem, 2011. 59(1): p. 145-51.
Giannakakou, P., et al., Low concentrations of paclitaxel induce cell type-dependent p53, p21 and G1/G2 arrest instead of mitotic arrest: molecular determinants of paclitaxel-induced cytotoxicity. Oncogene, 2001. 20(29): p. 3806-13.
Liu Z, G. Zhu, R.H. Getzenberg, and R.W. Veltri, the upregulation of PI3K/Akt and MAP kinase pathways is associated with resistance of microtubule-targeting drugs in prostate cancer. J Cell Biochem, 2015. 116:p. 1341-1349.
Burris, H.A., 3rd, Overcoming acquired resistance to anticancer therapy: focus on the PI3K/AKT/mTOR pathway. Cancer Chemother Pharmacol, 2013. 71(4): p. 829-42.
Wang, Z.W., Y.J. Huang, and J.Q. Zhang, Molecularly targeting the PI3K-Akt-mTOR pathway can sensitize cancer cells to radiotherapy and chemotherapy. Cellular & Molecular Biology Letters, 2014. 19(2): p. 233-242.
Wu, G., et al., AKT/ERK activation is associated with gastric cancer cell resistance to paclitaxel. International Journal of Clinical and Experimental Pathology, 2014. 7(4): p. 1449-1458.
Yoon, J.H., et al., Tangeretin reduces ultraviolet B (UVB)-induced cyclooxygenase-2 expression in mouse epidermal cells by blocking mitogen-activated protein kinase (MAPK) activation and reactive oxygen species (ROS) generation. J Agric Food Chem, 2011. 59(1): p. 222-8.
Vanhoecke, B.W., et al., A safety study of oral tangeretin and xanthohumol administration to laboratory mice. In Vivo, 2005. 19(1): p. 103-7.

* cited by examiner

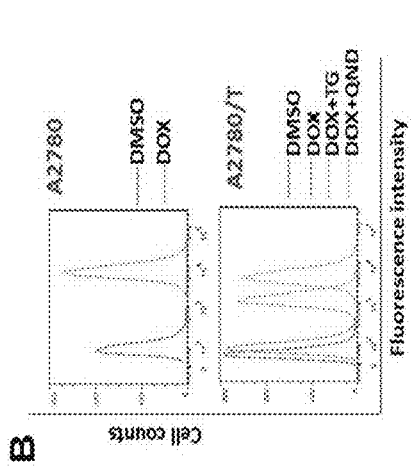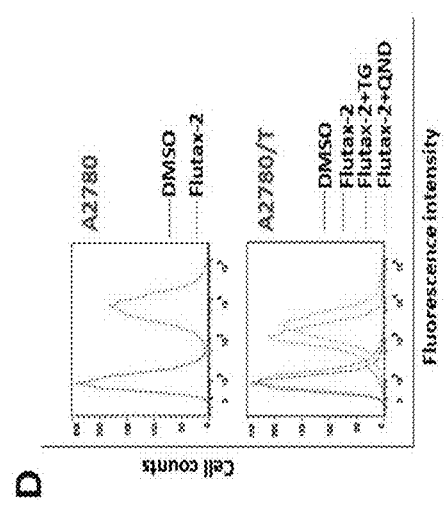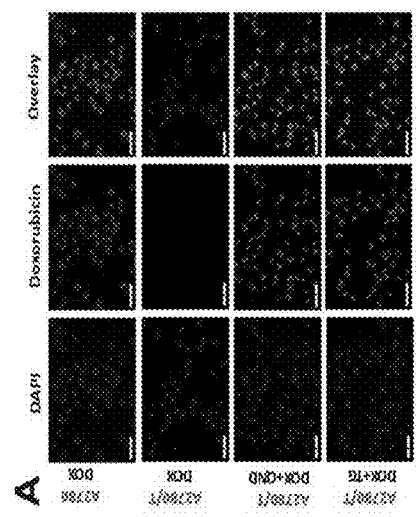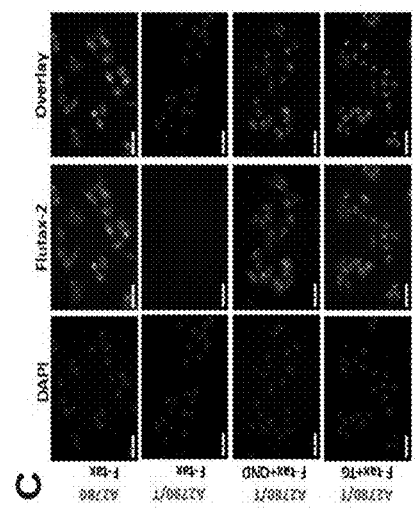
Fig. 5A
Fig. 5B
Fig. 5C
Fig. 5D

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Forward primer for MDR1

<400> SEQUENCE: 1
gagagatcct caccaagcgg                                          20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for MDR1

<400> SEQUENCE: 2

```
cgagcctggt agtcaatgct                                              20

<210> SEQ ID NO 3
<211> LENGTH: 20
<212> TYPE: DNA
<213> ORGANISM: Artificial Sequence
<220> FEATURE:
<223> OTHER INFORMATION: Forward primer for TIF

<400> SEQUENCE: 3
agaaggctgg ggctcatttg                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for TIF

<400> SEQUENCE: 4
aggggccatc cacagtcttc                                              20
```

USE OF TANGERETIN IN CANCER TREATMENT

CROSS-REFERENCE TO RELATED APPLICATION

This application claims benefit under 35 U.S.C. §119(e) of U.S. Provisional Application having Ser. No. 62/198,141 filed 29 Jul. 2015, which is hereby incorporated by reference herein in its entirety.

REFERENCE TO SEQUENCE LISTING

The hard copy of the sequence listing submitted herewith and the corresponding computer readable form are both incorporated herein by reference in their entireties.

FIELD OF INVENTION

This invention relates to a citrus methoxyflavone and the use thereof for treating cancer.

BACKGROUND OF INVENTION

Multidrug resistance (MDR) is the major cause of cancer chemotherapy failure, and remains an unsolved problem in clinic. The most established mechanism for MDR is the overexpression of ATP-binding cassette (ABC) family membrane transporters. Up to now, ABC transporters have 49 members, among which ABCB1, ABCG2 and ABCCs are known as the most important members that result in MDR in cancer cells.

ABCB1, also known as glycoprotein P (P-gp) encoded by MDR1 gene, was the first cloned human ABC transporter that can transport a large number of compounds including most chemotherapeutic drugs such as taxanes (e.g. paclitaxel (PTX) and docetaxel) and anthracyclines (e.g. doxorubicin (DOX) and mitoxantrone). In cancerous tissue, the expression of P-gp is usually highest in tumors that are derived from tissues that normally express P-gp, such as epithelial cells of the colon, kidney, adrenal, pancreas, and liver, resulting in the potential for resistance to some cytotoxic agents. Developing inhibitors that either down-regulate the expression of ABC proteins or inhibit the efflux function of ABC transporters would have potential clinical benefit as a "combination therapy strategy". However, the first, second and third generations of ABC modulators such as quinine, verapamil, cyclosporine-A, tariquitor, PSC 833, LY335979, and GF120918 required high doses to reverse MDR and were associated with adverse effects. These limitations have spurred efforts to search for new, more effective compounds from natural products with low toxicity and fewer side effects.

SUMMARY OF INVENTION

In the light of the foregoing background, it is an object of the present invention to provide an alternate composition in treating multidrug resistance cancer.

Accordingly, the present invention, in one aspect, is a pharmaceutical composition for treating multidrug resistance cancer, including a citrus methoxyflavone and a chemotherapeutic drug.

In an exemplary embodiment of the present invention, the citrus methoxyflavone can inhibit function of ABCB1 transporter such that intracellular accumulation of the chemotherapeutic drug is increased.

In another exemplary embodiment, the citrus methoxyflavone is tangeretin; the chemotherapeutic drug is paclitaxel, docetaxel, doxorubicin or daunorubicin. In yet another exemplary embodiment, the multidrug resistance cancer is paclitaxel-resistant cancer; in a further exemplary embodiment, the paclitaxel-resistant cancer is non-small cell lung cancer or paclitaxel-resistant ovarian cancer.

According to another aspect of the present invention, a method of treating multidrug resistance cancer is provided that includes administrating a pharmaceutically effective amount of a citrus methoxyflavone and a chemotherapeutic drug to a subject in need thereof.

In an exemplary embodiment of the present invention, the citrus methoxyflavone can inhibit function of ABCB1 transporter such that intracellular accumulation of the chemotherapeutic drug is increased.

In another exemplary embodiment, the citrus methoxyflavone is tangeretin; the chemotherapeutic drug is paclitaxel, docetaxel, doxorubicin or daunorubicin. In yet another exemplary embodiment, the multidrug resistance cancer is paclitaxel-resistant; in a further exemplary embodiment, the paclitaxel-resistant cancer is non-small cell lung cancer or paclitaxel-resistant ovarian cancer.

In another exemplary embodiment, the citrus methoxyflavone is tangeretin; the chemotherapeutic drug is paclitaxel, docetaxel, doxorubicin or daunorubicin. In yet another exemplary embodiment, the multidrug resistance cancer is paclitaxel-resistant non-small cell lung cancer or paclitaxel-resistant ovarian cancer.

In a further aspect, the present invention provides a method of enhancing the efficacy of a chemotherapeutic drug in treating multidrug resistance cancer, including (a) administering said chemotherapeutic drug to the subject; and (b) applying a citrus methoxyflavone.

In an exemplary embodiment of the present invention, the citrus methoxyflavone can inhibit function of ABCB1 transporter such that intracellular accumulation of the chemotherapeutic drug is increased.

In another exemplary embodiment, the citrus methoxyflavone is tangeretin; the chemotherapeutic drug is paclitaxel, docetaxel, doxorubicin or daunorubicin. In yet another exemplary embodiment, the multidrug resistance cancer is paclitaxel-resistant; in a further exemplary embodiment, the paclitaxel-resistant cancer is non-small cell lung cancer or paclitaxel-resistant ovarian cancer.

In a further aspect of the present invention, a method of sensitizing ABCB1-ovexpressing cells to chemotherapeutic drug in the treatment of multidrug resistance cancer, comprising the administration of tangeretin to a subject in need thereof.

In another exemplary embodiment, the chemotherapeutic drug is paclitaxel, docetaxel, doxorubicin or daunorubicin. In yet another exemplary embodiment, the multidrug resistance cancer is paclitaxel-resistant non-small cell lung cancer or paclitaxel-resistant ovarian cancer.

In another exemplary embodiment, the citrus methoxyflavone is tangeretin; the chemotherapeutic drug is paclitaxel, docetaxel, doxorubicin or daunorubicin. In yet another exemplary embodiment, the multidrug resistance cancer is paclitaxel-resistant non-small cell lung cancer or paclitaxel-resistant ovarian cancer.

BRIEF DESCRIPTION OF FIGURES

The patent or application file contains at least one drawing executed in color. Copies of this patent or patent application publication with color drawing(s) will be provided by the Office upon request and payment of the necessary fee.

As shown in FIG. 2A and FIG. 2B, tangeretin reduces the $IC_{50}$ value of paclitaxel in resistant cancer cells (A2780/T) but not in drug sensitive cancer cells (A2780). In FIG. 2C, tangeretin reduces the $IC_{50}$ value of paclitaxel in resistant cancer cells (A549/T), where cells were treated with the indicated drugs for 48 hours and subjected to SRB assay. Lastly, colony formation assay of PTX in the presence or absence of tangeretin was shown in FIG. 2D. Colony numbers were counted after Giemsa staining using the software of Quantity one-Colony counting. $IC_{50}$ values are represented as mean±SD of three independent experiments performed in triplicate. ## or , P<0.01., ### or *, P<0.001, significantly different from those obtained in the absence of tangeretin.

FIG. 3 shows the percentage of proportion of apoptosis cells. The data is representative of three different experiments and shown as mean±SD (n=3). ## or , P<0.01., ### or *, P<0.001, significantly different from those obtained in the absence of tangeretin.

FIG. 4 shows the distribution of cells in the cell cycle. Representative histograms indicate the percentages of cells in the G0/G1, S and G2/M phases of the cell cycle with the average values (±S.D.). Data is representative of three different experiments. ## or , P<0.01., ### or *, P<0.001.

FIG. 5A, FIG. 5B, FIG. 5C and FIG. 5D show the effect of tangeretin on intracellular accumulation of doxorubicin (DOX) and flutax1-2(F-tax) in drug-resistant ovarian cancer cells (A2780/T) and drug sensitive cells (A2780). A2780 cells or A2780/T cells treated with 5 µM DOX (with results shown in FIG. 5A and FIG. 5B) or 5 µM F-tax (with results shown in FIG. 5C and FIG. 5D) for 8 hours in the absence or presence of 7.53 µM tangeretin, and 20 µM quinidine (positive control) as indicated. Intracellular DOX and F-tax accumulations were observed with a florescence microscope (with results shown in FIG. 5A and FIG. 5C) or evaluated by measuring florescence with flow cytometry (with results shown in FIG. 5B and FIG. 5D) as described below, for example Section 2.5. The experiments were repeated for at least 3 times and representative images are shown.

FIG. 6A and FIG. 6C show the effect of tangeretin on the directional transport of DOX (10 µM) and Rho123 (5 µM) across Caco-2 cell monolayers, whereas FIG. 6B and FIG. 6D illustrate the effects of tangeretin on the efflux ratio of DOX (10 µM) and Rho123 (5 µM) in Caco-2 cell monolayers. Data represents the mean±SD of three individual determinations in which data in the presence of tangeretin is significantly different from those obtained in the absence of tangeretin. □ AP→BL transport, ■ BL→AP transport. ## or , P<0.01., ### or *, P<0.001.

As shown in FIG. 8A, the MDR1 mRNA level was determined by RT-PCR, whereas equal amounts of total lysate were loaded and detected by Western blot as shown in FIG. 8B. Tangeretin did not influence either MDR1 mRNA level or P-gp expression level, but unregulated the p53 expression. The experiments were performed three times.

FIG. 9A shows the cartoon style of the homology model of human ABCB1 in which the binding poses of QZ59-RRR (green) and tangeretin (orange) are shown in site 1. FIG. 9B shows the interaction between tangeretin and the surrounding residues. The red dotted line represents hydrogen bond between atoms, while the yellow dotted line represents π-π stacking between aromatic rings. Important amino acids are depicted as sticks with the atoms colored as carbon—green, hydrogen—white, nitrogen—blue, oxygen—red, whereas tangeretin is shown with the same color scheme as above except carbon atoms are represented in orange. FIG. 9C shows an interaction sketch between tangeretin and its binding site. Residues are shown as colored bubbles, cyan indicates polar and green indicates hydrophobic residues. Hydrogen bond is shown by purple dotted arrow.

DETAILED DESCRIPTION OF THE PREFERRED EMBODIMENTS

As used herein and in the claims, "comprising" means including the following elements but not excluding others.

Figure 1:
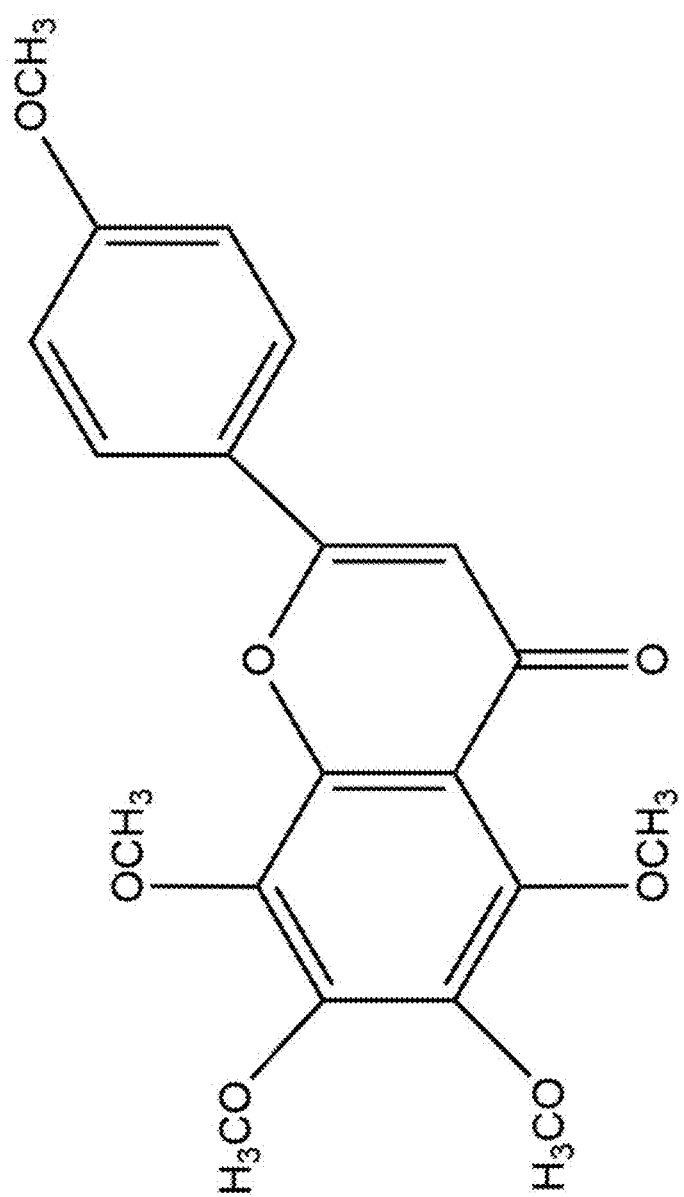
FIG. 1 shows the chemical structure of tangeretin.

Flavonoid is a large group of poly-phenolic antioxidant found in fruits and vegetables. Much evidence indicates that flavonoids interact with ABC transporters and modulate MDR in tumors. In their previous studies, the inventors have screened a self-built library comprising flavonoids from natural products or Chinese herbs against human ovarian paclitaxel resistance cancer cell A2780/T to identify the most suitable candidates. Tangeretin (5,6,7,8,4'-pentamethoxyflavone), as shown in FIG. 1, stands out as a potential candidate. Tangeretin is a non-toxic dietary bioflavonoid found in citrus peel (Citrus sinensis) as well as orange juice and it was reported to exhibit biological effects via its anti-inflammatory, anti-tumor, cholesterol lowering, and neuroprotective activities.

In view of the aforesaid, the objectives of this invention are 1) to determine the effects of tangeretin on ABCB1 mediated MDR at nontoxic concentrations; and 2) to illustrate the underlying mechanism(s).

1. Materials and Methods

1.1 Reagents and Cell Culture

Tangeretin was purchased from Dalian Meilun Biology Technology Co., Ltd, and the structure and purity was confirmed by LC-MS by the inventors. PTX, verapamil (Vrp), quinidine and other chemicals were purchased from Sigma-Aldrich (St. Louis, Mo.). Flutax-2 was purchased from Life Technologies. Stock solutions of tangeretin (40 mM), DOX (40 mM) and PTX (80 mM) were prepared in dimethyl sulfoxide (DMSO) and appropriate working concentrations were prepared in cell culture medium immediately before use. The RPMI 1640 medium, fetal bovine serum, penicillin and streptomycin were obtained from Life Technologies Inc. (Grand Island, N.Y.). DMSO, RNase A, leupeptin, aprotinin, phenyl methyl sulfonyl fluoride, Triton X-100 and PI were purchased from SigmaAldrich Co. (St Louis, Mo.). Actin antibody was purchased from Santa Cruz Biotechnology, USA, while P-gp and P53 antibodies were purchased from Calbiochem and Abcam.

Human ovarian cancer cells A2780 and its PTX-resistant cell line A2780/T, human non-small cell lung cancer (NSCLC) A549 and its PTX-resistant cell line A549/T were generously provided by Professor Zhi-Hong Jiang (Macau University of science and technology, Macau). Cells were grown as monolayers in RPMI-1640 medium supplemented with 10% fetal bovine serum (GIBCO, Paisley, Scotland) at 37° C. in a humidified 5% CO2 atmosphere. The indicated concentration of paclitaxel (0.94 µM) was added to the culture medium to maintain drug resistance for A2780/T and A549/T. The There was no significant changes in the mRNA level after grown in drug-free culture medium for 10 days for both resistant cell lines. The human colon carcinoma cell line Caco-2 was purchased from the ATCC, and cells at passage numbers 25-35 were used for the assays.

1.2 Cell Cytotoxicity Assay

Sulphorhodamine B (SRB) assays were carried out as previously described to assess cell density, based on sensitive measure of total cellular protein, which performed similarly compared with other proliferation assays such as MTT assay. Briefly, cells were seeded into flat bottomed 96-well plates at an initial density of $7.5 \times 10^3$ per well before treatment. Cells were exposed to varying concentrations of tangeretin (7.53, 2.51 and 0.83 µM) and combined with varying concentrations of PTX (1 µM to 0.03 nM with 3.16 fold diluted, 10 µM to 0.3 nM with 3.16 fold diluted, 100 µM to 3 nM with 3.16 fold diluted respectively) were added to the exposed cells to test whether this combination can enhance the growth inhibition of MDR cancer cells. After removing the medium, cells were fixed in 10% trichloroacetic acid for 1 h at 4° C. and then washed with water five times. 0.4% SRB dissolved in 1% v/v acetic acid was added and incubated 30 mm for staining. The cells were quickly washed with 1% acetic acid and left to dry overnight. The protein bound SRB was solubilized by adding 200 µl 10 mM Tris buffer per well and measured at wavelengths 490 nm using a plate reader (Spectra MAX 250; Molecular Devices, Sunnyvale, Calif.). The optical density of SRB in each well is directly proportional to the cell number. The degree of resistance was estimated by comparing the $IC_{50}$ (concentration of 50% inhibition) for the MDR cells to that of parent sensitive cells; while, the degree of reversal of MDR was calculated by dividing the $IC_{50}$ for cells with the chemotherapeutic drugs in the absence of tangeretin by that obtained in the presence of tangeretin.

For the colony formation assays, A2780/T or A549/T cells (200 cells/well) in 6-well plates were treated with culture medium (containing 0.94 µM paclitaxel for maintaining resistance) or combined with tangeretin in different concentration (containing 0.94 µM paclitaxel) for 12 days. Subsequently, the cells were fixed with 70% ethanol and stained with crystal violet (0.5% in ethanol). The plates were rinsed with phosphate buffered saline (PBS), and the colony numbers were counted using the software of Quantity one-Colony counting.

1.3 Cell Cycle Analysis

A2780/T cells were harvested after 24-hours, 48-hour, or 72-hour treatment and washed twice with ice-cold PBS. The cells were fixed and permeabilized with 70% ice-cold ethanol overnight at 4° C. or −20° C. for 2 h. After one additional wash in PBS, cells were stained with a staining solution containing PI (50 µl/ml) and RNase A (250 µg/ml) for 30 mM at room temperature. They were then pelleted, washed and suspended in PBS to a final concentration of $1 \times 10^6$/ml and analyzed by flow cytometry (BD FACS Aria, BD Biosciences, San Jose, Calif.).

1.4 Apoptosis Analysis by Annexin-V/PI Double-Staining Assay

After treatment, $1 \times 10^6$ cells were collected, washed and suspended in 100 µl of binding buffer (10 mM N-2-hydroxyethylpiperazine-N,-2-ethanesulfonic acid/NaOH, 140 mM NaCl, 2.5 mM CaCl2, pH 7.4). Apoptotic cells were identified by double supravital staining with 5 µl recombinant FITC (fluorescein isothiocyanate)-conjugated Annexin-V and 5 µl PI (50 µg/ml). The cells were stained for 15 mM at room temperature in the dark, and analyzed by fluorescence-activated cell sorting cater-plus flow cytometry. Data acquisition and analysis were performed in BD FACS Aria with FlowJo software.

1.5 Combination Index in Tangeretin Combination Studies

The synergistic therapeutic effect of tangeretin in combination of PTX was evaluated by using the Chou-Talalay Method. Drug resistant A2780/T cells were exposed to a serially diluted mixture of tangeretin ($IC_{50}$=36.35 µM) and PTX ($IC_{50}$=2.51 µM) for 48 hours. The 2-fold serial solutions with several concentration points above and below its $IC_{50}$ value were used for evaluating cytotoxicity of combination by SRB assay as described above. Combination index (CI) was calculated to quantitatively depict synergistic (CI<D, additive (CI=1), or antagonistic (CI>1) effect. With the use of CalcuSyn software v. 2.1 (Bio-soft), synergy is further refined as synergism (combination index=0.3-0.7), strong synergism (combination index=0.1-0.3), and very strong synergism (combination index<0.1).

1.6 Intracellular Accumulation of Doxorubicin and Flutax-2

1.6.1 Fluorescence Microscopy Observation

A2780 or A2780/T cells ($5 \times 10^6$) were cultured on the cover glass (ISO LAB 20×20 mm). DOX (5 µM), or flutax-2(1 µM) (active fluorescent taxoid) with or without the addition of tangeretin (7.53 µM) was added and incubated for 8 h. After treatment, cells were fixed in 4 wt % formaldehyde (Sigma-Aldrich). Nuclear DNA was stained with 1 µg/mL blue-fluorescent DAPI (1 mg/mL in H2O stock solution; Invitrogen D1306). One drop of fluorescent preservation solution (fluorsave reagent, CALBIOCHEM) was added before observation. Imaging was carried out for comparing the intracellular accumulation of DOX and flutax-2 with a Fluorescence Microscopy (Leica DM2500, Leica, Germany).

1.6.2 Flow Cytometry Analysis

Flutax-2(1 µM) and DOX (5 µM) were added to A2780 or A2780/T cells and incubated in the presence or absence of tangeretin (7.53 µM) for 8 h. Cells were detached, resuspended in 500 µl of PBS after washed twice with cold PBS, and analyzed by flow cytometry (BD FACS Aria, BD Biosciences, San Jose, Calif.). Excitation and emission wavelengths (nm) used for DOX and flutax-2 were as follows: 480 to 585; and 496 to 524. Quinidine (QND, 20 µM), a known ABCB1 inhibitor, was used as a positive control.

1.7 Transport Assay in Caco-2 Monolayer Model

The Caco-2 cell line was seeded on Millipore Millicell plates and formed a confluent monolayer over 21 days prior to the experiment. The integrity of the cell monolayers was checked by measuring the transepithelial electrical resistance (TEER) before and after the transport experiments using a WPI EVOM volt-ohmmeter fitted with STX2 chopstick electrodes (World Precision Instruments, Sarasota, Fla.). On Day 21, the transport assay included apical-to-basolateral (A→B) and basolateral-to-apical (B→A) transport rate determinations for rhodamin123 (5 µM) and DOX (10 µM) in Caco-2 cell line was carried out over a 2-hour time period. Briefly, samples (100 µL) were collected from apical/basolateral side of Caco-2 cell monolayer at predetermined times at the $30^{th}$, $60^{th}$, $90^{th}$ and $120^{th}$ min, and immediately detected for the fluorescence intensity in 96-well black plate (Corning; Cat. 3603) using a microplate reader (infinite M200 PRO, TECAN, Switzerland). For tangeretin inhibition studies, bidirectional transport of target compound was conducted in Caco2 cell monolayer with tangeretin added in both apical and basolateral chambers. Quinidine was used as potent control inhibitors of P-gp.

The apparent permeability coefficients (Papp) were calculated as $$P_{app} = \frac{dQ}{dt} \times \frac{1}{C_0 A}$$

Where dQ/dt (mM/sec) is the rate of permeation of compound across the cells, $C_0$ (MM) is the donor compartment concentration at time zero and A (cm$^2$) is the area of the cell monolayer. The decrease in Efflux Ratio (ER=$P_{app}$ (B to A)/$P_{app}$ (A to B)) in the presence of tangeretin and putative inhibitor quinidine (QND) was determined to assess their relative inhibitory potency to transporter P-gp.

1.8. ABCB1 ATPase Activity Assay

The impact of tangeretin on P-gp ATPase activity was estimated by Pgp-Glo™ assay systems (Promega, USA). The inhibitory effects of tangeretin were also examined against a verapamil-stimulated ABCB1 ATPase activity. Sodium orthovanadate (Na$_3$VO$_4$) was used as an ABCB1 ATPase inhibitor. In accordance with the manufacture's instruction, 0.25 mM Na$_3$VO$_4$, 0.5 mM verapamil, or tangeretin in various concentrations were incubated with assay buffer, 25 µg recombinant human ABCB1 membranes and 5 mM MgATP at 37° C. for 40 min. For examination of the inhibitory effects of tangeretin against verapamil-stimulated Pgp ATPase activity, 200 µM verapamil was added together with tangeretin. Luminescence was initiated by ATP detection buffer. The plate (white opaque 96-well, corning, USA) was further incubated at room temperature for 20 mM to develop luminescent signal, and was read with luminometer (infinite M200 PRO,TECAN, Switzerland). The changes of relative light units (ΔRLU) were determined by comparing Na$_3$VO$_4$-treated samples with tangeretin only or tangeretin and verapamil combination-treated samples, and hence, the ATP consumed was obtained by comparing to a standard curve.

1.9 RT-PCR Analysis

RT-PCR was performed to evaluate MDR1 mRNA expression. mRNA from cell lysates were purified by binding to poly(dT) magnetic beads (Life technologies) and reverse transcribed by using SuperScript II (Life technologies). Standard quantitative RT-PCR was performed in duplicates at least two to three times by using SYBR Green (Molecular Probes) protocols on the ViiA™ 7 Real-Time PCR System (Life technologies). The primer sequences: 5'-GAGAGATCCTCACCAAGCGG-3' (SEQ ID 325 NO:1) and 3'-CGAGCCTGGTAGTCAATGCT-5' (SEQ ID NO:2) for MDR1, and 5'-AGAAGGCTGGGGCTCATTTG-3' (SEQ ID NO:3) and 3'-AGGGGCCATC-CACAGTCTTC-5' (SEQ ID NO:4) for control gene eukaryotic translation initiation factor (TIF). RT-PCR data was normalized by measuring average cycle threshold (Ct) ratios between candidate genes and control gene TIF.

1.10 Western Blot Analysis

The total cellular samples were harvested and rinsed twice with ice-cold PBS buffer. Cell extracts were lysed in RIPA buffer (50 mM Tris (pH 7.4), 150 mM NaCl, 1% Triton X-100, 1% sodium deoxycholate, 0.1% SDS, sodium orthovanadate, sodium fluoride and EDTA) containing protease inhibitor cocktails (Roche Life Science, USA). Protein concentration was determined using the BCA protein assay kit. Equal amounts of cell lysates were resolved by SDS-PAGE and subsequently electrophoretically transferred onto PVDF membranes (Millipore, Darmstadt, Germany). After blocking in tris-buffered saline containing 0.1% of Tween20 (TBST) with 5% (w/v) skim milk (Nestle Carnation, New Zealand) for 2 h at room temperature, the membranes were incubated with primary and secondary antibodies and subsequently visualized with an enhanced chemiluminescence detection kit (Thermo Scientific™ SuperSignal™ West Pico Chemiluminescent Substrate, USA). β-Actin was used as the loading control for the experimental data analysis.

1.11. Molecular Modeling—ABCB1

In order to figure out the exact binding site for tangeretin, homology modeling and molecular docking were used to study the interaction between human P-Glycoprotein and tangeretin.

Based on the assumption that human P-glycoprotein (ABCB1) has four sites interacting with the inhibitors, the inventors rebuilt the four sites using Prime v2.1 in Maestro 9.0 (Schrodinger, Inc., New York, N.Y., 2009). The 3D structures of ABCB1 from the mouse were selected as the templates: the complex structure co-crystallized with QZ59-RRR (PDB: 4M25) for site 1; the complex structure co-crystallized with QZ59-SSS (PDB: 4M2T) for site 2; and the apo structure (PDB: 3G5U) for site3 and site 4. The ligands from the complex templates were retained and used to define the site 1 and the site 2 in the homology structures. The site 3 was defined by residues contributing to verapamil binding and the site 4 was defined by two residues which were common to the other three sites.

All the docking calculations for the four sites were performed in the Induced Fit Docking module (Schrodinger, Inc., New York, N.Y., 2009) and the pose was ranked by the XP mode of Glide program v5.5 (Schrodinger, Inc., New York, N.Y., 2009). Then the poses with the highest docking were selected for further conformational analysis.

1.12 Statistical Analysis

Microsoft Excel 2010 and GraphPad Prism 5.00 software were used in data processing and analyzing. Statistical analysis was carried out using Student's t-test or one-way analysis of variance. The statistical significance was determined to be P<0.05 (*), P<0.01 () or P<0.001(*). Data was expressed as the mean±SD.

2. Results 2.1 Sensitizing of ABCB1-Overexpressing Cells to Chemotherapeutic Agents by Tangeretin The results of the study on the effect of tangeretin on the paclitaxel sensitivity of resistant cancer cells (A2780/T and A549/T) and drug sensitive cells (A2780) were illustrated in FIG. 2A, FIG. 2B, FIG. 2C and FIG. 2D.

The stably paclitaxel-resistant cell line (A2780/T, cultured with 0.94 µM PTX to maintain drug resistance) exerted much higher tolerance than their parental sensitive cell line (A2780) with mean $IC_{50}$ values for PTX and DOX being 501-fold and 158-fold greater in A2780/T cells than that of A2780. The intrinsic cytotoxicity of tangeretin was measured in A2780 and A2780/T by the SRB assay. Tangeretin has similar $IC_{50}$ values for A2780 and A2780/T (culture medium without 0.94 µM PTX) which were 35.57 and 36.35 µM, respectively. Notably, the results showed that tangeretin at 7.53 µM had no obvious cytotoxic effect to all cell lines, and more than 90% cells were survived. Based on this observation, tangeretin was tested in the reversal assays at a maximum concentration of 7.53 µM.

Figures 2A, 2B, 2C, 2D:
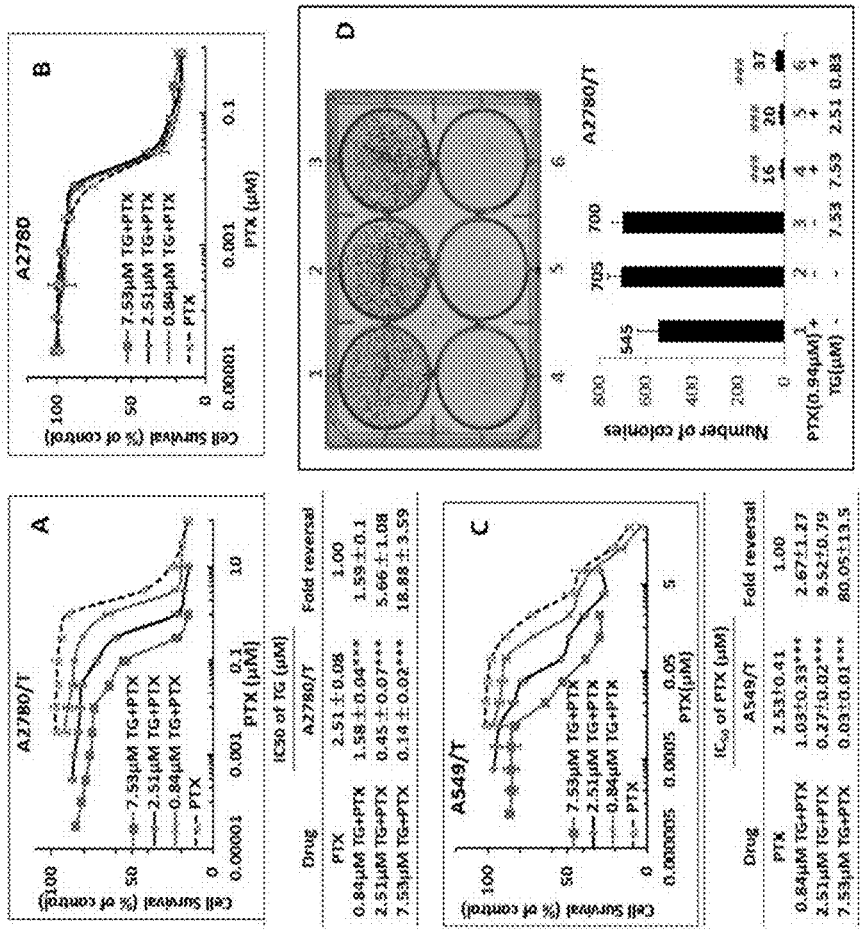
FIG. 2A, FIG. 2B, FIG. 2C and FIG. 2D show the effect of tangeretin on the paclitaxel resistant cancer cells (A2780/T and A549/T) and paclitaxel sensitive cells (A2780).

Next, the inventors tested whether tangeretin could reverse ABCB1 mediated drug resistance in A2780 and A2780/T. Treatment with tangeretin significantly decreased the $IC_{50}$ of PTX in A2780/T cell lines in a concentration-dependent manner, as shown by a shift in the cytotoxicity curves to the left in FIG. 2A. Specifically, as shown in Table 1, treatment with 0.84, 5.21, and 7.53 µM tangeretin reduced the $IC_{50}$ value of PTX by 1.59-, 5.66-, and 18.88-fold, respectively in A2780/T cells. However, tangeretin had no effect on the $IC_{50}$ value of PTX in parental non-resistant A2780 cells as shown in FIG. 2B. Moreover, at concentration of 7.53 µM, tangeretin also reduced $IC_{50}$ values of docetaxel, DOX, and daunorubicin with reversal fold of 33.66, 10.00 and 8.03 respectively, whereas it also slightly decreased the $IC_{50}$ values of 5-fluorouracil (non-substrate of ABCB1) with reversal fold of 6.31.

TABLE 1

Tangeretin reverses the ABCB1-mediated drug resistance to chemotherapeutic agents in A2780/T and A549/T cells.

| Drug | A2780/T | | A549/T | |
|---|---|---|---|---|
| | $IC_{50} \pm SD$ (µM) | fold reversal | $IC_{50} \pm SD$ (µM) | fold reversal |
| Paclitaxel | 2.51 ± 0.08 | 1.00 | 2.53 ± 0.41 | 1.00 |
| +0.84 µM TG | 1.58 ± 0.04 | 1.59 | 1.03 ± 0.33* | 2.67 |
| +5.21 µM TG | 0.45 ± 0.07* | 5.66 | 0.27 ± 0.02** | 9.52 |
| +7.53 µM TG | 0.14 ± 0.02** | 18.88 | 0.03 ± 0.01*** | 80.05 |
| Docetaxel | 28.37 ± 4.59 | 1.00 | 12.68 ± 2.06 | 1.00 |
| +0.84 µM TG | 14.22 ± 2.31* | 1.99 | 7.80 ± 1.29 | 1.58 |
| +5.21 µM TG | 3.57 ± 0.58** | 7.95 | 3.36 ± 0.28* | 3.82 |
| +7.53 µM TG | 0.84 ± 0.07*** | 33.66 | 1.06 ± 0.08** | 12.07 |
| Doxorubicin | 6.35 ± 1.03 | 1.00 | 7.13 ± 1.15 | 1.00 |
| +0.84 µM TG | 3.98 ± 0.65 | 1.58 | 4.74 ± 0.38 | 1.50 |
| +5.21 µM TG | 2.00 ± 0.33* | 3.16 | 2.38 ± 0.19* | 2.99 |
| +7.53 µM TG | 0.63 ± 0.11** | 10.00 | 1.06 ± 0.08** | 6.79 |
| Daunorubicin | 7.51 ± 0.61 | 1.00 | 6.70 ± 0.54 | 1.00 |
| +0.84 µM TG | 5.66 ± 0.92 | 1.34 | 4.74 ± 0.38 | 1.41 |
| +5.21 µM TG | 3.4 ± 0.82* | 2.25 | 2.99 ± 0.24* | 2.25 |
| +7.53 µM TG | 0.96 ± 0.23** | 8.03 | 1.06 ± 0.08** | 6.36 |
| 5-Fluorouracil | 179.01 ± 29.02 | 1.00 | 142.19 ± 23.05 | 1.00 |
| +0.83 µM TG | 151.86 ± 36.73 | 1.19 | 106.1 ± 8.63 | 1.34 |
| +2.51 µM TG | 84.28 ± 6.56* | 2.12 | 66.95 ± 5.44* | 2.12 |
| +7.53 µM TG | 28.37 ± 4.60* | 6.31 | 23.76 ± 1.93** | 6.05 |

In another ABCB1-overexpressing non-small cell human lung cancer cell line A549/T (PTX-resistance) and its parental cells A549, similar reversal effects of tangeretin to PTX was observed. In FIG. 2C, the addition of tangeretin significantly decreased the $IC_{50}$ value of PTX with reversal fold of 2.67, 9.52, and 80.05 in combination with 0.84, 2.51, and 7.53 µM tangeretin, respectively. Further, as shown in Table 1, treatment with 0.83, 5.21, and 7.53 µM tangeretin reduced the $IC_{50}$ value of PTX by 2.67-, 9.52-, and 80.05-fold, respectively in A2780/T cells.

In short, the results of this study suggest that tangeretin significantly sensitizes ABCB1-overexpressing cells to chemotherapeutic drugs.

2.2 Potentiating PTX Induced Apoptosis in Resistant A2780/T Cells by Tangeretin

Figure 3:
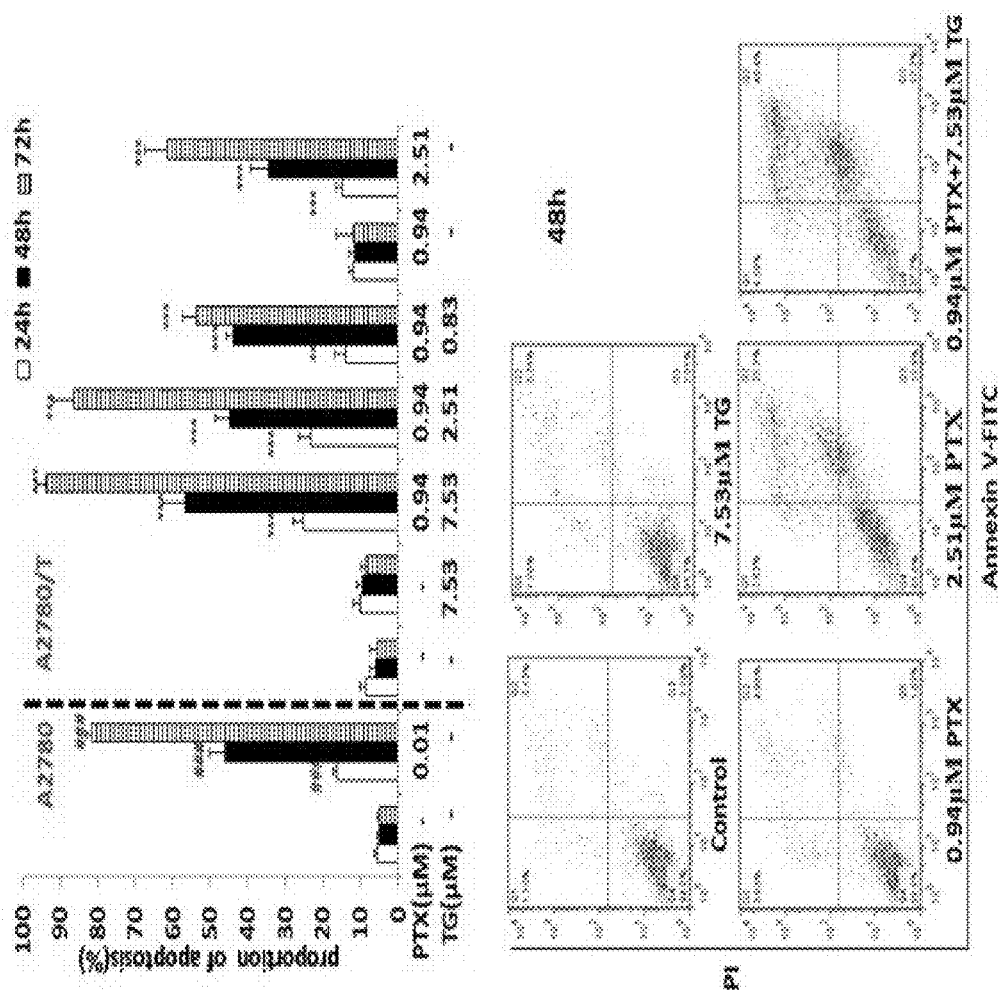
FIG. 3 shows the effect of the tangeretin-PTX combination on apoptotic induction in A2780 and A2780/T cells. The cells were treated with PTX and/or tangeretin for 24 h, 48 h, 72 h and co-stained with propidium iodide (PI) and fluorescein isothiocyanate-conjugated annexin V.

Next, a study was conducted to investigate whether tangeretin can increase the PTX-induced apoptosis in A2780 and A2780/T cells using double staining method. Consistent with its ability to inhibit cell growth, treatment with 0.83, 2.51 and 7.53 µM tangeretin could significantly increase apoptosis induced by 0.94 µM PTX in a concentration-dependent manner, as shown in FIG. 3. It was observed that treatment with only 0.83 µM tangeretin could boost apoptosis induced by PTX (0.94 µM) to a similar induction as that of 2.51 µM PTX ($IC_{50}$), while single treatment of 7.53 µM tangeretin or 0.94 µM PTX did not show apoptosis induction.

To further confirm these results, the well-established biochemical markers of cell cycle and apoptosis: p53 were examined. Consistent with cell growth inhibition and apoptosis, treatment of PTX in combination with tangeretin resulted in accumulation of p53 in treated cells as shown FIG. 8B.

2.3 Arrest of Resistant Cells in G2/M-Phase by Tangeretin-PTX Combination

In this study was, the inventors investigated whether the effect of tangeretin causing G2/M cell cycle arrest is related to their observed synergistic effect between tangeretin and PTX. The results of this study were illustrated in FIG. 4.

Asynchronously growing A2780/T cells and its sensitive parental cell line A2780, treated with PTX in the absence or presence of tangeretin, were examined for their cell cycle progression by flow cytometry. In untreated control, the percentage of A2780 cells in G0/G1-, S- and G2/M-phases were 62.23%, 19.23% and 16.90%, respectively, while the percentage of A2780/T cells in G0/G1-, S- and G2/M-phases were 66.40%, 14.10% and 16.73%, respectively. For A2780 cells, single exposure (24, 48, and 72 hours) with PTX (0.01 µM) resulted in G2 arrest, manifested by an increased G2-M content (52.63%, 62.33% and 74.20%), and decreased G1 phase content (30.95%, 14.13% and 13.07%, respectively).

Figure 4:
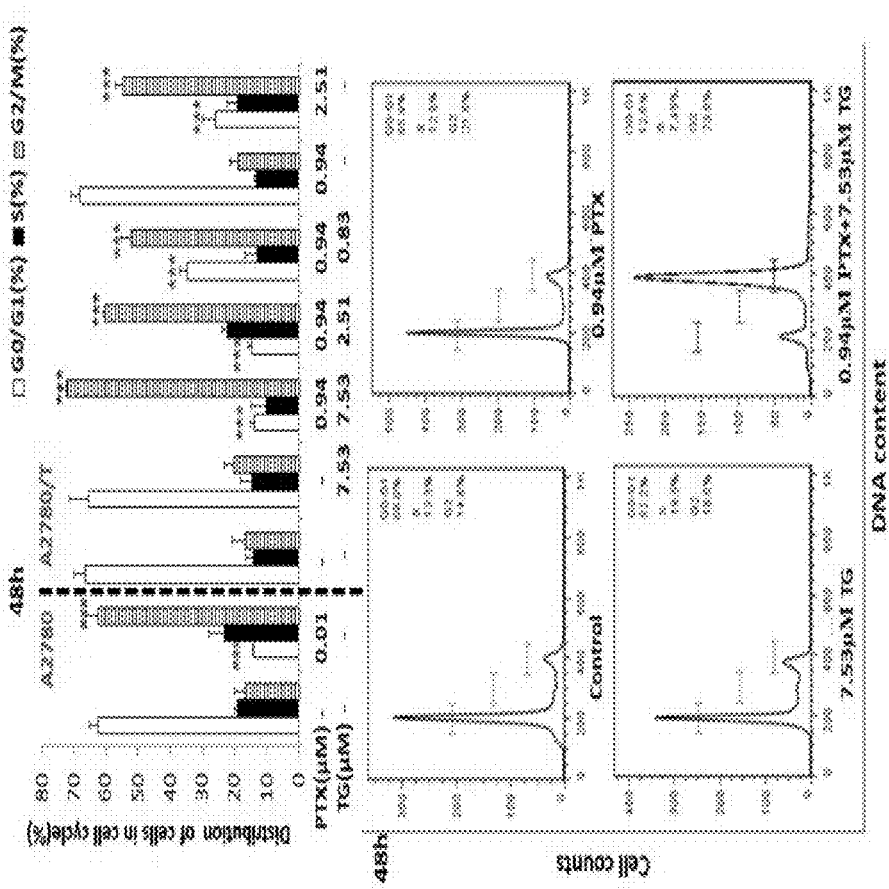
FIG. 4 shows the effect of the tangeretin-PTX combination on cell cycle in A2780 and A2780/T cells. The cells were treated with PTX and tangeretin for 48 h and then fixed and stained with PI. The cell cycle distribution profiles of the cells were determined by flow cytometry

In the absence of tangeretin treatment, there were 68.30% G1 phase and 18.87% G2 phase cells incubated with 0.94

μM PTX, whereas at 7.53 μM tangeretin in combination with 0.94 μM PTX this distribution significantly shifted to 13.87% G1 and 72.37% G2 phase cells after treatment of 48 h in A2780/T cells as further illustrated in FIG. 4. This pattern was evidenced after 24 h and persisted over 72 h of the treatment (N.B. such data was not shown in FIG. 4). Also shown in FIG. 4, a notable G2/M arrest was observed even at the lowest concentration of tangeretin tested (0.83 μM). Thus, while A2780/T cells were remarkably resistant to PTX, the combination of tangeretin with PTX was found to greatly increase the proportion of G2/M arrested cells to above 70%. However, tangeretin (7.53 μM) alone had no effect on the cell cycle of A2780/T.

In short, the results of this study suggest that tangeretin-PTX combination induces G2/M arrest in A2780/T cells.

2.4 Evaluation of Combinational Effects for Tangeretin and PTX

The combinational cytotoxic effect of tangeretin with PTX in A2780/T cells was evaluated by the CalcuSyn software and the results thereof were shown in Table 2 below. The combination index (CI) values computed at 50% and 90% cell kill were 0.098 (CI at $ED_{50}$) and 0.003 (CI at $ED_{90}$), indicating strong synergistic cytotoxic effect for combinations of tangeretin with PTX in the ABCB1-overexpressing A2780/T cells. With CalcuSyn simulation, an $ED_{50}$ is produced by 67.45 μM tangeretin or 3.61 μM PTX alone in A2780/T cells, but a combination of agents will produce $ED_{50}$ at 0.20 μM PTX with 2.84 μM tangeretin, an 18-fold decrease for the $ED_{50}$ dose of PTX in Table 2.

TABLE 2

The values of CI and the synergistic dose of tangeretin and PTX at Fa 0.5 (ED50)

| Data for Fa = 0.5 | CI value | Dose tangeretin (μM) | Dose PTX(μM) |
|---|---|---|---|
| Tangeretin | / | 67.45 | / |
| PTX | / | / | 3.61 |
| Tangeretin and PTX | 0.098 | 2.84 | 0.20 |

Note:
CI analyses of the effects of tangeretin in combination with paclitaxel are shown. The CI values were plotted as a function of the particular inhibitory effect. CI values <1 represent a synergistic combination, CI values equal to 1 indicate an additive effect whereas CI values >1 represent antagonistic combinations.

Further, it can be concluded from Table 2 that the dosage of PTX was significantly reduced in tangeretin treated A2780/T cells.

In short, this evaluation study confirms the synergistic effect in the combinational use of tangeretin and PTX in cancer treatment.

2.5 Increase of the Intracellular Accumulation of DOX and Flutax-2 by Tangeretin The results from the studies discussed above proved that tangeretin had a significant effect on reversing ABCB1-mediated MDR. At present, the mechanism of this phenomenon is unknown. Therefore, the inventors conducted assays to examine the effect of tangeretin on the accumulation of DOX, and Flutax-2 (a fluorescent taxol derivative) in A2780 cells and their corresponding ABCB1-overexpressing A2780/T cells.

The study on the effect of tangeretin on the intracellular accumulation of DOX and Flutax-2 was carried out by using fluoresce microscope and flow cytometry analysis. As shown in FIG. 5A, FIG. 5B, FIG. 5C and FIG. 5D, the intracellular accumulation of DOX and Flutax-2 were significantly higher in A2780 than that of A2780/T. When the drug-resistant cells were treated with 7.53 μM tangeretin or 20 μM QND (positive control), the intracellular accumulations of DOX (as shown in FIG. 5A) and Flutax-2 (as shown in FIG. 5C) were higher than that of untreated A2780/T. In contrast, tangeretin had no effect on DOX and Flutax-2 levels in parental A2780 cells. With flow cytometry analysis, the enhanced intracellular accumulation of DOX and Flutax-2 by tangeretin was further confirmed as respectively shown in FIG. 5B and FIG. 5D.

Taken together, these results showed that tangeretin significantly increased the intracellular accumulation of chemotherapeutic drugs in ABCB1-overexpressing cells, thus increased the cytotoxicity to these MDR cells. In other words, tangeretin is shown to enhance the efficacy of DOX or PTX in MDR cancer treatment.

2.6 Inhibition of the Efflux Activity of ABCB1 Transporter in Caco-2 Cells by Tangeretin Caco-2 cells derived from human colorectal carcinoma are widely used as an in vitro model for predicting human drug absorption and efflux activity of transporters. To further confirm the effect of tangeretin on P-gp function, the $P_{app}$ and efflux ratio (the ratio between the $P_{app}$ from the BL to the AP side and that from the AP to the BL side) of the P-gp substrates Rho 123, DOX, in the presence or absence of tangeretin were evaluated using the Caco-2 monolayer model. The results of this study were illustrated in FIG. 6A and FIG. 6B.

Figure 6A:
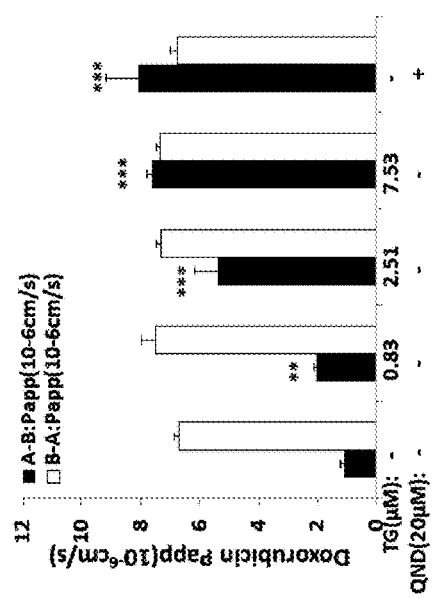
FIG. 6A, FIG. 6B, FIG. 6C and FIG. 6D show that tangeretin increases the adsorption and inhibits the efflux ratio of DOX and Rho123 in Caco-2 cells.
Figure 6B:
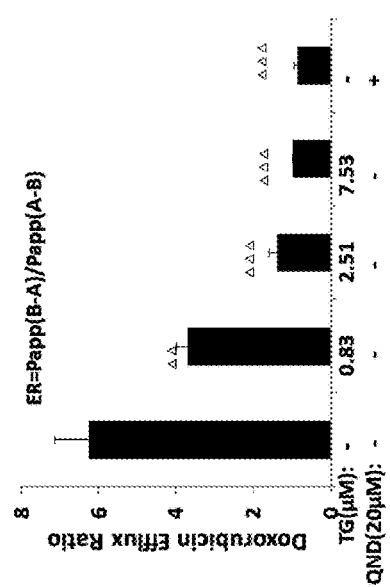
Figure 6C:
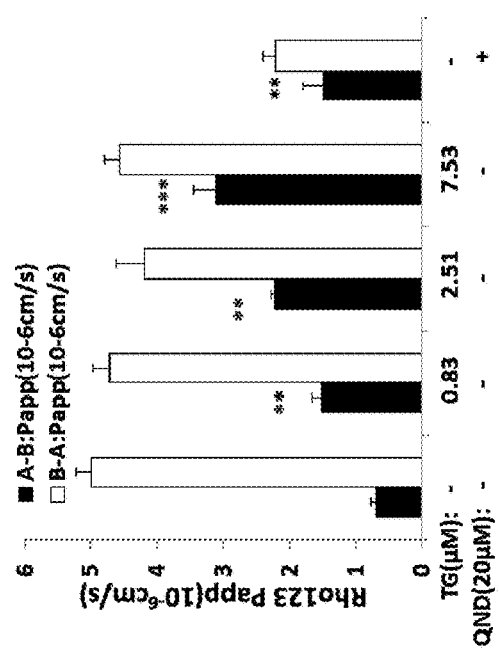
Figure 6D:
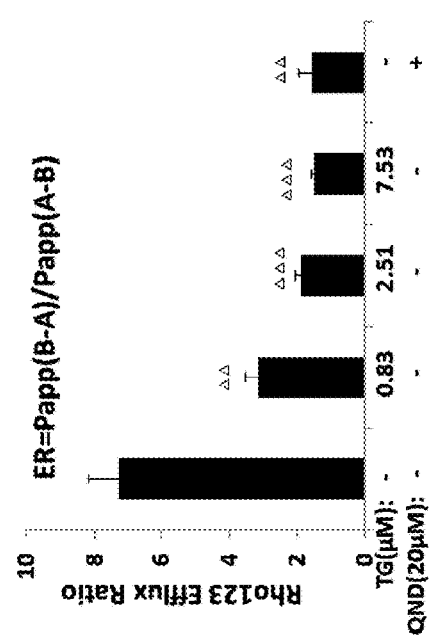

Two hours after administration, the $P_{app}$ (A-B) of DOX (as shown in FIG. 6A) and Rho 123 (as shown in FIG. 6C) were increased from A to B side in the presence of tangeretin in a dose-dependent fashion. Further, the efflux ratio was decreased in a tangeretin concentration dependent manner. As shown in FIG. 6B, the mean efflux ratio of DOX was decreased about 1.23-fold, 4.27-fold and 6.81-fold with tangeretin concentration of 0.84, 2.51 and 7.53 μM, respectively. Intriguingly, the inhibitory effect of tangeretin at 2.51 μM was stronger than that of 20 μM QND (positive control). These results were in agreement with the notion that tangeretin increased Rho 123, DOX, accumulation in resistant ABCB1-overexpressing cells by inhibiting ABCB1 transporter.

In short, the decrease of efflux ratio of DOX in the presence of tangeretin suggested that tangeretin is shown to increase absorption of DOX into Caco-2 cells by effecting the ABCB1 transporter function.

2.7 Activation of the ATPase Activity of ABCB1 by Tangeretin

ABC transporters mediate the transport of substrates against a concentration gradient using energy derived from ATP hydrolysis, which is proportional to the transporter activity. Therefore, we measured ABCB1-mediated ATP hydrolysis with different concentrations of tangeretin was measured and the results thereof are shown in FIG. 7A and FIG. 7B.

Figure 7A:
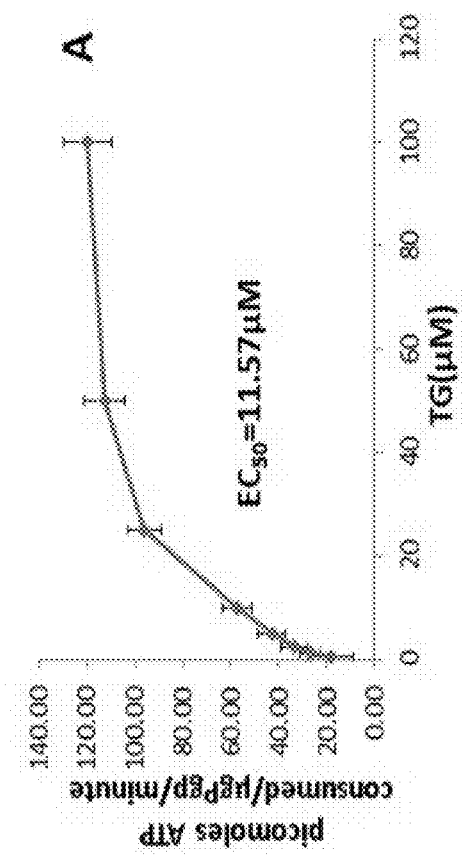
FIG. 7A and FIG. 7B show the capacity of tangeretin (TG) on stimulating P-gp ATPase activity and on inhibiting 200 µM verapamil-stimulated P-gp ATPase activity. $EC_{50}$ measurements for stimulating P-gp ATPase activity by tangeretin were shown in FIG. 7A, whereas $IC_{50}$ measurements for inhibiting 200 µM verapamil-stimulated P-gp ATPase activity by tangeretin were shown in FIG. 7B. Luminescence was read on a luminometer and data was analyzed as described below, for example Section 2.8.
Figure 7B:
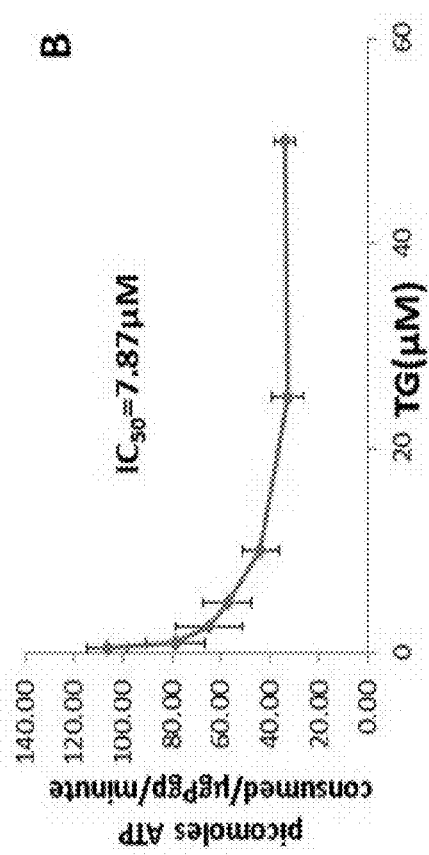

As shown in FIG. 7A, tangeretin stimulated the ATPase activity of ABCB1 in a dose-dependent manner, with $EC_{50}$ at 11.57 μM and a maximal stimulation of 3-fold of the basal activity. This result suggests that tangeretin affects the ATPase activity of ABCB1 and may interact at the drug-substrate-binding site as a substrate of ABCB1.

To characterize inhibition effect of tangeretin on P-gp ATPase activity, the effects of tangeretin on verapamil stimulated P-gp ATPase activity was also examined Verapamil is sometimes referred as a P-gp inhibitor because acting as a substrate for transport, it inhibits P-gp activity with other substrates by interfering with their transport in a competitive mode. FIG. 7B shows the reduction of 200 μM verapamil-stimulated ATPase activity by tangeretin with an $IC_{50}$ value of 7.87 μM, indicating that tangeretin is a P-gp ATPase inhibitor.

2.8 Mechanism of Reversal of ABCB1-Mediated MDR by Tangeretin

The reversal of ABCB1-mediated MDR can be achieved either by reducing ABCB1 expression or by inhibiting the function of ABCB1 transporter. Therefore, the effects of tangeretin on the expression of ABCB1 both at mRNA and protein level were investigated and the results thereof are shown in FIG. 8A and FIG. 8B.

Figure 8A:
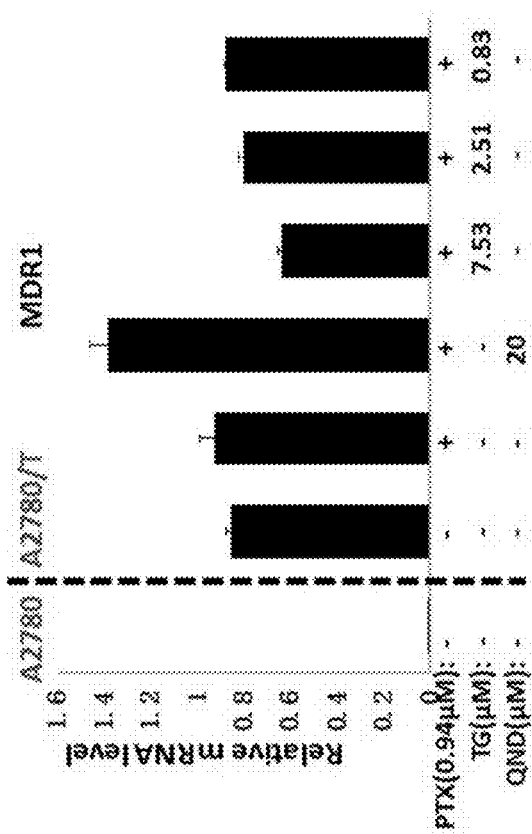
FIG. 8A and FIG. 8B show the effect of tangeretin on ABCB1 and p53 expression in MDR ovarian cancer cells. A2780/T cells or A2780 cells were treated with tangeretin at various concentrations for 48 hours.
Figure 8B:
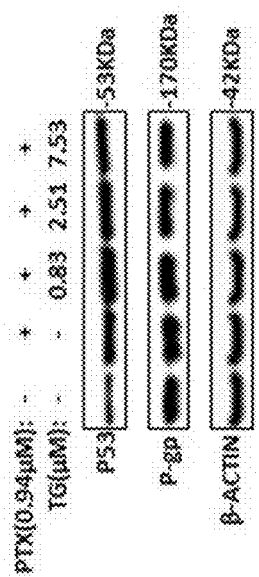

At the reversal concentrations (0.83-7.53 μM), tangeretin did not alter the mRNA (as shown in FIG. 8A) or protein level of ABCB1 (as shown in FIG. 8B) in A2780/T cells. These findings revealed that the MDR reversal effect of tangeretin was not due to the inhibition of ABCB1 expression. Therefore, the result suggested that the inhibition of ABCB1 transporter function appears to be the mechanism for the sensitization effect of tangeretin in MDR cells, and such inhibition leads to an increase in intracellular accumulation of chemotherapeutic drugs.

2.9 Molecular Docking Simulation of Tangeretin within the Drug Binding Cavity of ABCB1

To understand the binding mechanism of tangeretin to homology model 28 of human ABCB1 at molecular level, the inventors performed glide docking using ABCB1-QZ59-RRR (site-1), ABCB1-QZ59-SSS (site-2), ABCB1-verapamil (site-3), and site common to above three sites (site-4) and ATP binding site. According to the docking result, the poses of tangeretin were only accommodated to site 1 with Docking score (Kcal/mol) at −9.216. There were no poses suitable for tangeretin to bind to the other three sites. Thus, site 1 was the only rational site for tangeretin.

Figures 9A, 9B, 9C:
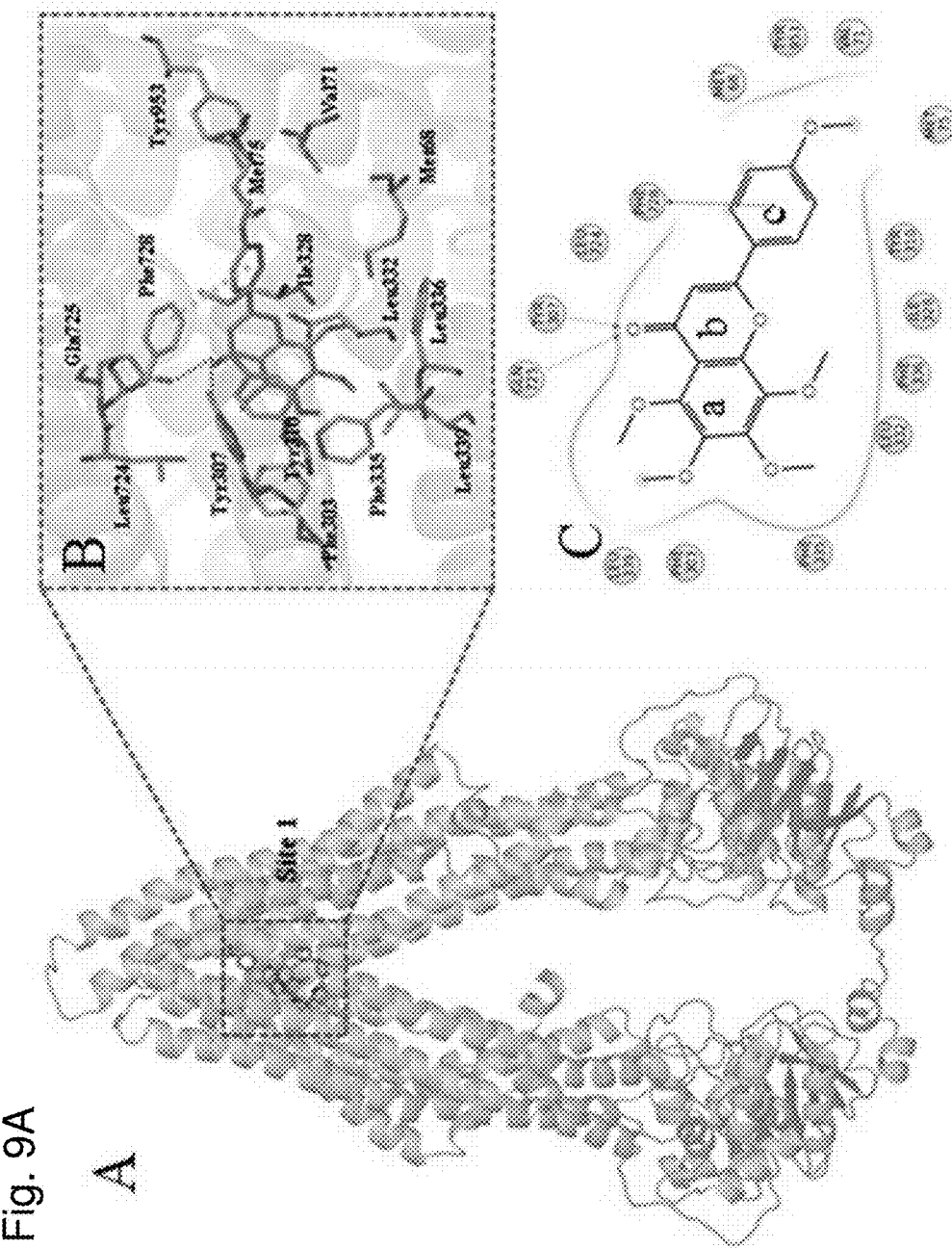
FIG. 9A, FIG. 9B and FIG. 9C illustrate the docking analysis of tangeretin with human ABCB1 homology model.

As shown in FIG. 9A, the binding site of tangeretin was partially superposed with the binding site of QZ59-RRR known as Site 1. The ring-a of tangeretin substituted with four methoxyl groups was mainly engaged in hydrophobic contacts with Tyr307, Phe303, Tyr310, Phe335, Leu339, Leu336, Leu332. The carbonyl of ring-b formed two hydrogen bonds with Tyr 307 and Gln725, which also appeared in the binding of vardenafil and tadalafil. As for ring-c, the π-π stacking with Phe728 and the hydrophobic contacts with Tyr953, Met75, Val71 kept the conformation stable.

3. Discussion

Chemotherapeutic agents such as PTX and DOX are widely used for the treatment of advanced human cancers, but long-term treatment leads to drug resistance even they are initially effective. Great efforts were made on searching for new effective resistance modulator targeting on efflux pumps with low toxicity and fewer side effects.

A wide variety of phytochemicals from natural resources, such as flavonoids, have been suggested to protect us from cancer (chemopreventives) or enhance the tumoricidal effects of chemotherapy (chemosensitizers). Strategies using combination of chemotherapeutic agents with highly promising dietary flavonoids for reversal MDR in cancer therapy represent the most useful alternatives for achieving higher curability with least toxicity.

In this invention, the inventors investigated the reversing effect of tangeretin, a citrus flavonoid, on the ABCB1-mediated drug resistance to chemotherapeutic agents as well as the underlying mechanism. It is the first time that tangeretin was demonstrated, at achievable nontoxic plasma concentrations, to significantly sensitize ABCB1-ovexpressing cells to chemotherapeutic agents including DOX, PTX, docetaxel and daunorubicin.

Tangeretin was selected from a screen of potential P-gp inhibitors because of its high efficiency in the preliminary experiments of this study, as well as its greater potential to reach target tissues and low toxicity. The synergistic effects of tangeretin on increasing the cytotoxic effect of cisplatin or doxorubicin have been reported at superphysiological doses. Previous pharmacokinetic studies have shown that $C_{max}$ of tangeretin is only around 1-5 μM in human and in rat. Thus the in vivo plasma concentration of tangeretin is far below the concentration (100-150 μM) used in these combination treatment to resistant cancer cells, indicating that these in vitro observed effects of tangeretin may not be achieved in vivo.

However, in this study, at achievable nontoxic plasma concentrations, tangeretin had strong reversal effect in ABCB1 overexpressing resistance cells. It significantly increased the cellular toxicity of ABCB1 substrates in A2780/T and A549/T cells (as shown in, for example, FIG. 2A, FIG. 2B, FIG. 2C and FIG. 2D and Table 1) by using SRB assays and colon formation assays. But tangeretin has no effect on the $IC_{50}$ of the parental A2780 and A549 cells. Consistent with the results of toxicity assays, treatment with tangeretin at non-cytotoxic concentrations promoted cell apoptosis induced by PTX (as shown in FIG. 3) in a p53-dependent manner. Although tangeretin has been reported to induce G2/M arrest in p53-null HL-60 promyelocytic leukemia cells, the inventors observed an accumulation of G2/M phase (>70%) in PTX-tangeretin co-treated resistant A2780/T cancer cells, whereas tangeretin (7.53 μM) alone had no effect on the cell cycle (as shown in FIG. 4). Moreover, the CI values indicated a strong synergistic cytotoxic effect for combination of tangeretin with PTX in the ABCB1-overexpressing A2780/T cells, which was further demonstrated with an 18-fold decrease in the $ED_{50}$ dose of PTX by using CalcuSyn simulation (as shown in Table 2). These results were in accordance with that of the cytotoxicity assays, in which tangeretin was proven to be able to increase the sensitivity of MDR cells to chemotherapeutic agents.

To elaborate the mechanism of the reversal effect, the inventors investigated whether tangeretin could inhibit the efflux of ABCB1 to enhance the cytotoxicity of agents by increasing the intracellular drug concentration. The inventors observed that tangeretin remarkably enhanced the intracellular accumulation of DOX and Flutaxel-2 in drug resistant cells by fluorescence microscopy and flow cytometry (FIG. 5A, FIG. 5B, FIG. 5C and FIG. 5D), while tangeretin did not significantly alter the levels of these agents in the parental sensitive cells. Moreover, tangeretin significantly reduced the efflux ratio of ABCB1 substrates including Rho123 and DOX in a Caco-2 monolayer cell model, indicating that it could inhibit the efflux activity of ABCB1 transporter (FIG. 6A and FIG. 6B). Importantly, the inhibiting effect of tangeretin (at 2.51 μM) on the efflux activity of ABCB1 was even more potent than that of QND (at 20 μM). Based on the above results, the inventors thus presumed that the reversal effect of tangeretin may result from inhibition of the efflux function of ABCB1 transporter.

One of the major reasons to inhibit the activity of ABCB1 transporter activity is to deplete ATP. As energy used by ABCB1 transporter comes from ATP hydrolysis, both activation and inhibition of transporters can be investigated by measuring ATPase activity using mammalian cell membranes containing high levels of human ABCB1 transporter.

Thus, the inventors studied the ATPase activity of ABCB1 transporter to confirm their previous assumption. In this study, the inventors found that tangeretin stimulated ATPase activity of ABCB1 transporter in a concentration-dependent manner with $EC_{50}$ at 11.57 µM (as shown in FIG. 7A), suggesting that tangeretin may be a substrate of ABCB1 transporter. Moreover, it inhibited verapamil-stimulated ATPase activity in a concentration-dependent manner (as shown in FIG. 7B), suggesting that tangeretin may be an inhibitor of ABCB1 ATPase. Although the activity of ATPase was increased, the efflux function of ABCB1 was inhibited accordingly by tangeretin. One of the possible reasons for this observation could be that tangeretin may competitively bound to the substrate-binding site of ABCB1, leaving little place for other agents to bind to the transporter, which resulted in a decreased activity of ABCB1 transporter as well as an enhanced intracellular drug concentration.

The reversal effect can be achieved either by reducing ABCB1 expression or by inhibiting the efflux ability of ABCB1 transporter. Therefore, the inventors further examined the effect of tangeretin on the expression of MDR1 mRNA and ABCB1 protein. Results from reverse transcription-PCR (RT-PCR) and Western blot analysis showed that ABCB1 expression did not alter at the mRNA and protein levels in MDR A2780/T cells after incubation with tangeretin up to 48 h at the reversal concentrations (as shown in FIG. 8A and FIG. 8B).

To better understanding the important interactions of tangeretin in the active site of ABCB1 protein, docking simulation was performed in the ATP binding site of ABCB1. The predicted binding conformation of tangeretin within the large hydrophobic drug binding cavity (site-1) of human ABCB1 shows the major contributions of hydrophobic interactions (as shown in FIG. 9A, FIG. 9B and FIG. 9C). The methoxyl and aromatic ring are important for interaction with the drug-binding cavity of ABCB1 transporters. In general, docking simulation will be useful for understanding ligand-protein interactions and for future optimizing derivatives.

Several mechanisms of acquired MDR have been identified such as reduced apoptosis, advanced DNA damage repair mechanisms or altered drug metabolism. There may be other mechanisms that can also contribute to the sensitizing effect of tangeretin in ABCB1-overexpressing MDR cancer cells. Several important molecules and signaling pathways have been shown to contribute to the resistance of cancer cells to chemotherapeutic agents such as the PI3K/AKT/mTOR and MAP kinase signaling pathways. Moreover, inactivation of the AKT/ERK signaling pathway renders MDR cancer cells more sensitive to microtubule-targeting drugs such as PTX. As tangeretin has been demonstrated with inhibition effect on the pathways of PI3K/Akt and MAP kinase, therefore, the effect of tangeretin on AKT/ERK phosphorylation may also account for the reversal effect of tangeretin. This part of work was carrying out in the inventors' lab which may help to explain the sensitizing effect of tangeretin to 5-fluorouracil.

In conclusion, this invention provides the first scientific evidence that tangeretin significantly enhances the efficacy of chemotherapeutic agents in ABCB1-overexpressing MDR cells by directly inhibiting ABCB1 drug efflux function. Moreover, the reversal effect of tangeretin is independent of inhibiting ABCB1 expression. The strong synergistic effects between tangeretin and chemotherapeutic agents were demonstrated in this study at clinically achievable non-toxic concentrations, indicating that combination use of tangeretin with may be a useful strategy to overcome MDR. Considering the broad-spectrum organ safety of tangeretin which has been demonstrated in animals in vivo, this invention should expedite the exploration and use of tangeretin in enhancing the efficacy of ABCB1 substrate chemotherapeutic agents in experimental animal studies as well as clinical trials. Moreover, it would also be appealing to determine whether tangeretin interacts with other chemotherapeutic agents in killing a variety of other drug-resistant cancer cells.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, one skilled in the art could appreciate that to achieve the synergistic effect mentioned in Section 2.4, the tangeretin could be applied together with PTX, or before/after PTX treatment.

What is claimed is:

1. A method comprising:
treating multidrug resistance cancer by administering a pharmaceutically effective amount of a citrus methoxyflavone and a chemotherapeutic drug to a subject in need thereof,
wherein the citrus methoxyflavone is tangeretin, the multidrug resistance cancer is paclitaxel resistant-ovarian cancer and the chemotherapeutic drug is paclitaxel;
wherein the paclitaxel and the tangeretin are administered to the subject in a molar ratio of 0.94:0.84 to 0.94:7.53 to treat the paclitaxel-resistant ovarian cancer.

2. The method of claim 1 wherein the tangeretin can inhibit function of ABCB1 transporter such that intracellular accumulation of the paclitaxel is increased.

3. The method of claim 1, wherein the molar ratio of the paclitaxel to the tangeretin is selected from a group consisting of 0.94:0.84, 0.94:5.21 and 0.94:7.53.

4. The method of claim 1, wherein the paclitaxel and the tangeretin are simultaneously administered to the subject.

5. A method comprising:
enhancing an efficacy of a chemotherapeutic drug in treating multidrug resistance cancer by administering the chemotherapeutic drug to a subject; and
applying a citrus methoxyflavone to the subject,
wherein the citrus methoxyflavone is tangeretin, the multidrug resistance cancer is paclitaxel resistant-ovarian cancer and the chemotherapeutic drug is paclitaxel;
wherein the paclitaxel and the tangeretin are administered to the subject in a molar ratio of 0.94:0.84 to 0.94:7.53 to treat the paclitaxel-resistant ovarian cancer.

6. The method of claim 5 wherein the tangeretin can inhibit function of ABCB1 transporter such that intracellular accumulation of the paclitaxel is increased.

7. The method of claim 5, wherein the molar ratio of the paclitaxel to the tangeretin is selected from a group consisting of 0.94:0.84, 0.94:5.21 and 0.94:7.53.

8. The method of claim 5, wherein the paclitaxel and the tangeretin are simultaneously administered to the subject.

* * * * *